(12) United States Patent
Steinhagen et al.

(10) Patent No.: US 8,263,621 B2
(45) Date of Patent: Sep. 11, 2012

(54) TARTRATE DERIVATIVES FOR USE AS COAGULATION FACTOR IXA INHIBITORS

(75) Inventors: Henning Steinhagen, Sulzbach (DE); Markus Follmann, Wulfrath (DE); Jochen Goerlitzer, Frankfurt am Main (DE); Herman Schreuder, Hofheim (DE)

(73) Assignee: Sanofi, Paris (FR)

( * ) Notice: Subject to any disclaimer, the term of this patent is extended or adjusted under 35 U.S.C. 154(b) by 369 days.

(21) Appl. No.: 12/400,187

(22) Filed: Mar. 9, 2009

(65) Prior Publication Data

US 2009/0233961 A1    Sep. 17, 2009

Related U.S. Application Data

(63) Continuation of application No. PCT/EP2007/007612, filed on Aug. 31, 2007.

(30) Foreign Application Priority Data

Sep. 13, 2006  (DE) .......................... 10 2006 042 927

(51) Int. Cl.
*A61K 31/47*  (2006.01)
(52) U.S. Cl. ..................................... 514/310
(58) Field of Classification Search .................. None
See application file for complete search history.

(56) References Cited

U.S. PATENT DOCUMENTS

| | | | |
|---|---|---|---|
| 5,073,362 A | 12/1991 | Blaszkiewicz et al. | |
| 2002/0151595 A1 | 10/2002 | Ries et al. | |

FOREIGN PATENT DOCUMENTS

| | | |
|---|---|---|
| WO | WO 94/22885 | 10/1994 |
| WO | WO 02/42273 A2 | 5/2002 |
| WO | WO 2004/072101 A2 | 8/2004 |

OTHER PUBLICATIONS

STN Search Report and Summary (Accession No. 1910:5205) (containing summary of Tingle et al (Journal of the American Chemical Society 31:1312-1319, 1910).*
Batt et al (Bioorg Med Chem 14:5269-5273, 2004).*
Wang et al (J Med Chem, 53:1465-1472, 2010).*
Weltermann et al, The risk of recurrent venous thromboembolism among patients with high factor IX levels, J. Thromb. and Haemost. 2003 (1) pp. 28-32.
Feuerstein et al, An Inhibitory Anti-factor IX Antibody Effectively Reduces Thrombus Formation in a Rat Model of Venous Thrombosis, Thromb. Haemost. 1999 (82) pp. 1443-1445.

* cited by examiner

*Primary Examiner* — Craig Ricci
(74) *Attorney, Agent, or Firm* — Serena Farquharson-Torres; Scully, Scott, Murphy & Presser, P.C.

(57) ABSTRACT

The invention relates to the compounds of formula I

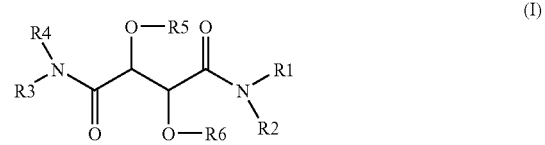

(I)

having antithrombotic activity which especially inhibits blood clotting factor IXa, to methods for producing the same and to the use thereof as drugs.

3 Claims, No Drawings

TARTRATE DERIVATIVES FOR USE AS COAGULATION FACTOR IXA INHIBITORS

The invention relates to novel compounds of the formula I having antithrombotic activity which, in particular, inhibit blood clotting factor IXa, to processes for their preparation and to use thereof as medicaments.

Blood clotting is a process of control of the blood stream essential for the survival of mammals. The process of clotting and the subsequent dissolution of the clot after wound healing has taken place commences after vascular damage and can be divided into four phases:

1. The phase of vasoconstriction or vasocontraction: By means of this the blood loss in the damaged area is decreased.
2. The next phase is platelet activation by thrombin. The platelets attach to the site of the vessel wall damage and form a platelet aggregate. The protein fibrinogen is responsible here for the crosslinkage of the platelets by means of appropriate surface receptors. Platelets also bind to exposed collagen of the extracellular matrix of the damaged vessel wall and are activated by this means. After activation of the platelets, a number of messenger substances are secreted, which induce the activation of further platelets. At the same time, a membrane lipid, phosphatidylserine, is transported from the inside of the membrane of the platelets to the outside, on which complexes of clotting factors can accumulate. The platelets accelerate blood clotting by means of this mechanism.
3. The formation of these clotting complexes leads to the massive formation of thrombin, which converts soluble fibrinogen to fibrin by cleavage of two small peptides. Fibrin monomers spontaneously form threadlike strands, from which, after crosslinkage by clotting factor XIII, a stable protein network forms. The initially even looser platelet aggregate is stabilized by this fibrin network; platelet aggregates and fibrin network are the two essential constituents of a thrombus.
4. After wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors.

The intrinsic pathway requires the clotting factors V, VIII, IX, X, XI and XII and also prekallikrein, high molecular weight kininogen, calcium ions and phospholipids from platelets.

The intrinsic pathway is initiated when prekallikrein, high molecular weight kininogen factor XI and XII bind to a negatively charged surface. This point in time is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, such that activation is the result. With increasing activation of factor XII, activation of factor XI occurs, which leads to a release of bradykinin, a vasodilator. As a result, the ending of the initial phase of vasoconstriction occurs. Bradykinin is formed from high molecular weight kininogen. In the presence of $Ca^{2+}$ ions, factor XIa activates factor IX. Factor IX is a proenzyme, which contains vitamin K-dependent, γ-carboxyglutamic acid (GLA) residues. The serine protease activity becomes noticeable after binding of $Ca^{2+}$ to these GLA residues. A number of the serine proteases of the blood clotting cascade (factors II, VII, IX and X) contain such vitamin K-dependent GLA residues. Factor IXa cleaves factor X and leads to activation to factor Xa. The prerequisite for the formation of factor IXa is the formation of a tenase complex from $Ca^{2+}$ and the factors VIIIa, IXa and X on the surface of activated platelets. One of the reactions of activated platelets is the presentation of phosphatidylserine and phosphatidylinositol along the surfaces. The exposure of these phospholipids first makes the formation of the tenase complex possible. Factor VIII in this process has the function of a receptor for the factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further and inactivated by thrombin. This dual activity of thrombin in relation to factor VII leads to a self-restriction of tenase complex formation and thus to a limitation of blood clotting.

The extrinsic pathway requires a tissue factor (TF) and clotting factors V, VII, VIII, IX and X. In the case of a vessel injury, the tissue factor (TF) accumulates with the clotting factor VII and the latter is activated. The complex of TF and clotting factor VII has two substrates, clotting factors X and IX.

Clotting factor IX can be activated by means of the intrinsic pathway and the extrinsic pathway. The activation of factor IXa is thus a central point of intersection between the two pathways of activation of clotting.

Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445).

The compounds of the formula I according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound of the formula I

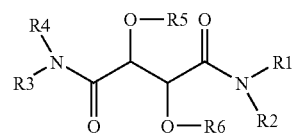

and/or all stereoisomeric forms of the compound of the formula I and/or mixtures of these forms in any ratio, and/or a physiologically tolerable salt of the compound of the formula I, where R1 is
1) —$(C_6-C_{14})$-aryl-Z, in which Z is a basic nitrogen-containing group and in which aryl is unsubstituted or mono-, di- or trisubstituted by T,
2) —$(C_3-C_{12})$-cycloalkyl-Z, in which Z is a basic nitrogen-containing group and in which cycloalkyl is unsubstituted or mono-, di- or trisubstituted by T,
3) a four- to fifteen-membered Het-Z, in which Z is a basic nitrogen-containing group and in which Het is unsubstituted or additionally mono-, di- or trisubstituted by T, R2 and R4 are identical or different and independently of one another are a hydrogen atom or —$(C_1-C_4)$-alkyl, R3 is
1) —$(C_0-C_4)$-alkylene-$(C_6-C_{14})$-aryl, in which aryl is unsubstituted or mono-, di- or trisubstituted by T,
2) —$(C_0-C_4)$-alkylene-Het, in which Het is unsubstituted or mono-, di- or trisubstituted by T,
3) —$(C_0-C_4)$-alkylene-$(C_6-C_{14})$-aryl-Q-$(C_6-C_{14})$-aryl, in which the two aryls in each case independently of one another are unsubstituted or mono-, di- or trisubstituted by T,
4) —$(C_0-C_4)$-alkylene-$(C_6-C_{14})$-aryl-Q-$(C_3-C_{12})$-cycloalkyl, in which aryl and cycloalkyl in each case independently of one another are unsubstituted or mono-, di- or trisubstituted by T,
5) —$(C_0-C_4)$-alkylene-$(C_6-C_{14})$-aryl-Q-Het, in which aryl and Het in each case independently of one another are unsubstituted or mono-, di- or trisubstituted by T,
6) —$(C_0-C_4)$-alkylene-Het-Q-$(C_6-C_{14})$-aryl, in which aryl and Het in each case independently of one another are unsubstituted or mono-, di- or trisubstituted by T, or
7) —$(C_0-C_4)$-alkylene-Het-Q-Het, in which the two Het radicals in each case independently of one another are unsubstituted or mono-, di- or trisubstituted by T, Q is a covalent bond, —$(C_1-C_4)$-alkylene, —NH—, —N(($C_1-C_4$)-alkyl)-, —O—, —$SO_2$— or —S—, T is
1) halogen,
2) —$(C_1-C_6)$-alkyl, in which alkyl is unsubstituted or independently mono, di- or trisubstituted by —$(C_1-C_3)$-fluoroalkyl, —N═C(O)—OH or —N═C(O)—$(C_1-C_4)$-alkyl,
3) —$(C_1-C_3)$-fluoroalkyl,
4) —$(C_3-C_8)$-cycloalkyl,
5) —OH,
6) —O—$(C_1-C_4)$-alkyl,
7) —O—$(C_1-C_3)$-fluoroalkyl,
8) —$NO_2$,
9) —CN,
10) —N(R10)(R11), in which R10 and R11 independently of one another are a hydrogen atom, —$(C_3-C_8)$-cycloalkyl, halogen or —$(C_1-C_6)$-alkyl,
11) —C(O)—NH—R10,
12) —NH—C(O)—R10,
13) —NH—$SO_2$—R10,
14) —$SO_2$—$(C_1-C_4)$-alkyl,
15) —$SO_2$—NH—R10,
16) —$SO_2$—$(C_1-C_3)$-fluoroalkyl,
17) —S—$(C_1-C_4)$-alkyl or
18) —S—$(C_1-C_3)$-fluoroalkyl, R5 and R6 are identical or different and independently of one another are a hydrogen atom, —C(O)—R12, —C(O)—O—R12, —C(O)—NH—R12 or —$(C_1-C_4)$-alkyl, where R12 is —$(C_1-C_6)$-alkyl, —$(C_3-C_8)$-cycloalkyl, —$(C_6-C_{14})$-aryl or Het.

The invention further relates to a compound of the formula I and/or all stereoisomeric forms of the compound of the formula I and/or mixtures of these forms in any ratio, and/or a physiologically tolerable salt of the compound of the formula I, where R1 is
1) —$(C_6-C_{14})$-aryl-Z, where aryl is selected from the group consisting of phenyl and naphthyl, and in which aryl is unsubstituted or mono-, di- or trisubstituted by T and Z is amino, aminomethylene, amidino, guanidino, azetidinyl, pyrrolidinyl, piperidinyl, pyridinyl or aminopyridinyl, or
2) a four- to fifteen-membered Het-Z, where Het is selected from the group consisting of acridinyl, azepinyl, azetidinyl, benzimidazolinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, beta-carbolinyl, quinazolinyl, quinolinyl, quinolizinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl or xanthenyl and in which Het is unsubstituted or mono-, di- or trisubstituted by T and in which Z is as defined above, R2 and R4 are identical or different and independently of one another are a hydrogen atom or —$(C_1-C_4)$-alkyl, R3 is
1) —$(C_0-C_4)$-alkylene-$(C_6-C_{14})$-aryl, in which aryl is as defined above and is unsubstituted or mono-, di- or trisubstituted by T,
2) —$(C_0-C_4)$-alkylene-$(C_6-C_{14})$-aryl-Q-$(C_6-C_{14})$-aryl, in which the two aryls in each case independently of one another are as defined above and in each case independently of one another are unsubstituted or mono-, di- or trisubstituted by T, 3) —($C_0$-$C_4$)-alkylene-($C_6$-$C_{14}$)-aryl-Q-($C_3$-$C_{12}$)-cycloalkyl, in which aryl is as defined above and cycloalkyl is unsubstituted or mono-, di- or trisubstituted by T, or
4) —($C_0$-$C_4$)-alkylene-($C_6$-$C_{14}$)-aryl-Q-Het, in which aryl and Het are as defined above and in each case independently of one another are unsubstituted or mono-, di- or trisubstituted by T, Q is a covalent bond, —($C_1$-$C_4$)-alkylene, —NH—, —N(($C_1$-$C_4$)-alkyl)- or —O—, T is
1) halogen,
2) —($C_1$-$C_6$)-alkyl, in which alkyl is unsubstituted or independently mono-, di- or trisubstituted by —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_6$)-cycloalkyl,
5) —OH,
6) —O—($C_1$-$C_4$)-alkyl,
7) —O—($C_1$-$C_3$)-fluoroalkyl,
8) —$NO_2$,
9) —CN,
10) —N(R10)(R11), in which R10 and R11 independently of one another are a hydrogen atom, —($C_3$-$C_6$)-cycloalkyl, halogen or —($C_1$-$C_6$)-alkyl,
11) —C(O)—NH—R10,
12) —NH—C(O)—R10,
13) —NH—$SO_2$—R10,
14) —$SO_2$—($C_1$-$C_4$)-alkyl,
15) —$SO_2$—NH—R10,
16) —$SO_2$—($C_1$-$C_3$)-fluoroalkyl,
17) —S—($C_1$-$C_4$)-alkyl or
18) —S—($C_1$-$C_3$)-fluoroalkyl, R5 and R6 are identical or different and independently of one another are a hydrogen atom, —C(O)—R12, —C(O)—O—R12, —C(O)—NH—R12 or —($C_1$-$C_4$)-alkyl, where R12 is —($C_1$-$C_6$)-alkyl, —($C_3$-$C_8$)-cycloalkyl, —($C_6$-$C_{14}$)-aryl or Het, and in which aryl and Het are as defined above.

The invention furthermore relates to a compound of the formula I and/or all stereoisomeric forms of the compound of the formula I and/or mixtures of these forms in any ratio, and/or a physiologically tolerable salt of the compound of the formula I, where R1 is carbamimidoylphenyl (benzamidino), aminomethylphenyl or Het-Z, where Het is selected from the group consisting of benzimidazolyl and isoquinolinyl, and in which Z is amino or amidino, R2 and R4 in each case are a hydrogen atom, R3 is
1) phenyl, in which phenyl is unsubstituted or mono- or disubstituted by T,
2) -phenyl-Q-phenyl, in which the two phenyl radicals in each case independently of one another are unsubstituted or mono- or disubstituted by T,
3) phenyl-Q-($C_3$-$C_6$)-cycloalkyl, in which phenyl and cycloalkyl in each case independently of one another are unsubstituted or mono- or disubstituted by T, or
4) phenyl-Q-Het-2, in which Het-2 is selected from the group consisting of quinolinyl, quinoxalinyl, furanyl, indolyl, isoquinolinyl, isothiazolyl, isoxazolyl, oxadiazolyl, piperidinyl, pyrazolyl, pyridazinyl, pyrimidinyl, pyridyl, pyrimidinyl, pyrrolyl, thiadiazolyl, thiazolyl, thienyl, thienopyrrolyl or thienothiophenyl and in whichphenyl and Het-2 in each case independently of one another are unsubstituted or mono- or disubstituted by T, Q is a covalent bond, —$CH_2$—, —N($CH_3$)— or —O—, T is
1) F, Cl or Br,
2) —($C_1$-$C_4$)-alkyl, in which alkyl are unsubstituted or independently mono- or disubstituted by —$CF_3$ or —N—C(O)—$CH_3$,
3) —$CF_3$,
4) —O—($C_1$-$C_4$)-alkyl,
5) —O—$CF_3$,
6) —$NO_2$,
7) —N(R10)(R11), in which R10 and R11 independently of one another are a hydrogen atom or —($C_1$-$C_4$)-alkyl, or
8) —$SO_2$—$CH_3$, R5 and R6 in each case are a hydrogen atom.

A further subject of the invention are compounds of the formula I from the group consisting of (2R,3R)—N-(1-aminoisoquinolin-6-yl)-2,3-dihydroxy-N'-p-tolyl-tartaramide,
(2R,3R)—N-(2-amino-3H-benzimidazol-5-yl)-2,3-dihydroxy-N'-p-tolyltartaramide,
(2R,3R)—N-(2-amino-3H-benzimidazol-5-yl)-N'-(4-cyclohexylphenyl)-2,3-dihydroxy-tartaramide,
(2R,3R)—N-(4-aminomethylphenyl)-2,3-dihydroxy-N'-p-tolylsuccinamide;
(2R,3R)—N-(4-carbamimidoylphenyl)-2,3-dihydroxy-N'-p-tolylsuccinamide,
(2R,3R)—N-(2-amino-3H-benzimidazol-5-yl)-N'-(4-fluorophenyl)-2,3-dihydroxy-tartaramide,
(2R,3R)—N-(2-amino-3H-benzimidazol-5-yl)-N'-(4-chlorophenyl)-2,3-dihydroxy-tartaramide,
(2R,3R)—N-(2-amino-3H-benzimidazol-5-yl)-2,3-dihydroxy-N'-phenyltartaramide,
(2R,3R)—N-(2-amino-3H-benzimidazol-5-yl)-2,3-dihydroxy-N'-(4-nitrophenyl)-tartaramide,
(2R,3R)—N-(2-amino-3H-benzimidazol-5-yl)-2,3-dihydroxy-N'-(4-isopropylphenyl)-tartaramide,
(2R,3R)—N-(2-amino-3H-benzimidazol-5-yl)-2,3-dihydroxy-N'-(4-piperidin-1-yl-phenyl)tartaramide or
(2R,3R)—N-(2-amino-3H-benzimidazol-5-yl)-2,3-dihydroxy-N'-(4-phenoxyphenyl)-tartaramide.

The term "—($C_1$-$C_4$)-alkyl" or "($C_1$-$C_6$)-alkyl" is understood as meaning hydrocarbon radicals whose carbon chain is straight-chain or branched and contains 1 to 4 or 1 to 6 carbon atoms, for example methyl, ethyl, propyl, isopropyl, butyl, isobutyl, tertiary-butyl, pentyl, isopentyl, neopentyl, hexyl, 2,3-dimethylbutane or neohexyl. The term "—($C_0$-$C_4$)-alkylene" is understood as meaning hydrocarbon radicals whose carbon chain is straight-chain or branched and contains 1 to 4 carbon atoms, for example methylene, ethylene, propylene, isopropylene, isobutylene, butylene or tertiary-butylene. "—$C_0$-Alkylene" is a covalent bond. The term "—($C_1$-$C_4$)-alkylene" is understood as meaning hydrocarbon radicals whose carbon chain is straight-chain or branched and contains 1 to 4 carbon atoms, for example methylene (—$CH_2$—), ethylene (—$CH_2$—$CH_2$—), propylene (—$CH_2$—$CH_2$—$CH_2$—), isopropylene, isobutylene, butylene or tertiary-butylene.

The term "—($C_3$-$C_{12}$)-cycloalkyl" is understood as meaning rings of 3 to 12 carbon atoms such as compounds which are derived from monocycles having 3 to 8 carbon atoms in the ring such as cyclopropane, cyclobutane, cyclopentane, cyclohexane, cycloheptane or cyclooctane, which are derived from the bicycles bicyclo[4.2.0]octane, octahydroindene, decahydronaphthalene, decahydroazulene, decahydrobenzocycloheptene or dodecahydroheptalene or from the bridged cycles such as spiro[2.5]octane, spiro[3.4]octane, spiro[3.5]nonane, bicyclo[3.1.1]heptane, bicyclo[2.2.1]heptane or bicyclo[2.2.2]octane.

The term "—($C_3$-$C_6$)-cycloalkyl" or "—($C_3$-$C_8$)-cycloalkyl" is understood as meaning radicals which are derived from monocycles having 3 to 6 or 3 to 8 carbon atoms in the ring such as cyclopropane, cyclobutane, cyclopentane, cyclohexane, cyclo-heptane or cyclooctane.

The term "—($C_6$-$C_{14}$)-aryl" is understood as meaning aromatic hydrocarbon radicals having 6 to 14 carbon atoms in the ring. —($C_6$-$C_{14}$)-Aryl radicals are, for example, phenyl, naphthyl, for example 1-naphthyl, 2-naphthyl, anthryl or fluorenyl. Naphthyl radicals and in particular phenyl radicals are preferred aryl radicals.

The term "four- to fifteen-membered Het" or "Het" is understood as meaning ring systems having 4 to 15 carbon atoms, which are present in one, two or three ring systems connected to one another and in which one, two, three or four identical or different heteroatoms from the group consisting of oxygen, nitrogen or sulfur can replace the respective carbon atoms. Examples of these ring systems are the radicals acridinyl, azepinyl, azetidinyl, benzimidazolinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, beta-carbolinyl, quinazolinyl, quinolinyl, quinolizinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl or xanthenyl.

The term "—($C_1$-$C_3$)-fluoroalkyl" is understood as meaning a partially or completely fluorinated alkyl radical which is derived, for example, from the following radicals —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "halogen" is understood as meaning fluorine, chlorine, bromine or iodine; fluorine, chlorine or bromine is preferred, in particular chlorine or bromine. The term "a basic nitrogen-containing group" is understood as meaning radicals where the conjugated acid of this group has a pKa of approximately 5 to 15. Examples of this basic nitrogen-containing group are amino, aminomethylene, amidino (carbamimidoyl), guanidino, azetidinyl, pyrrolidinyl, piperidinyl, pyridinyl or aminopyridinyl.

Functional groups of the intermediates used, for example amino or carboxyl groups, can be masked here by suitable protective groups. Suitable protective groups for amino functions are, for example, the t-butoxycarbonyl, the benzyloxycarbonyl, phthaloloyl, or the trityl or tosyl protective group. Suitable protective groups for the carboxyl function are, for example, alkyl, aryl or arylalkyl esters. Protective groups can be introduced and removed by techniques which are well-known or described here (see Green, T. W., Wutz, P. G. M., *Protective Groups in Organic Synthesis* (1991), 2nd Ed., Wiley-Interscience, or Kocienski, P., *Protecting Groups* (1994), Thieme). The term protective group can also include polymer-bound protective groups. Such masked compounds according to formula (I), in which, for example, the functional groups of the radicals U, V, X or W can optionally also be masked, can, although optionally themselves not pharmacologically active, optionally be converted after administration to mammals by metabolization to the pharmacologically active compounds according to the invention.

The compounds according to the invention can be prepared by well-known processes or according to processes described here.

The invention furthermore relates to a process for the preparation of the compound of the formula I and/or of a stereoisomeric form of the compound of the formula I and/or of a physiologically tolerable salt of the compound of the formula I, which comprises preparing the compound of the formula I according to Scheme 1.

Scheme 1:

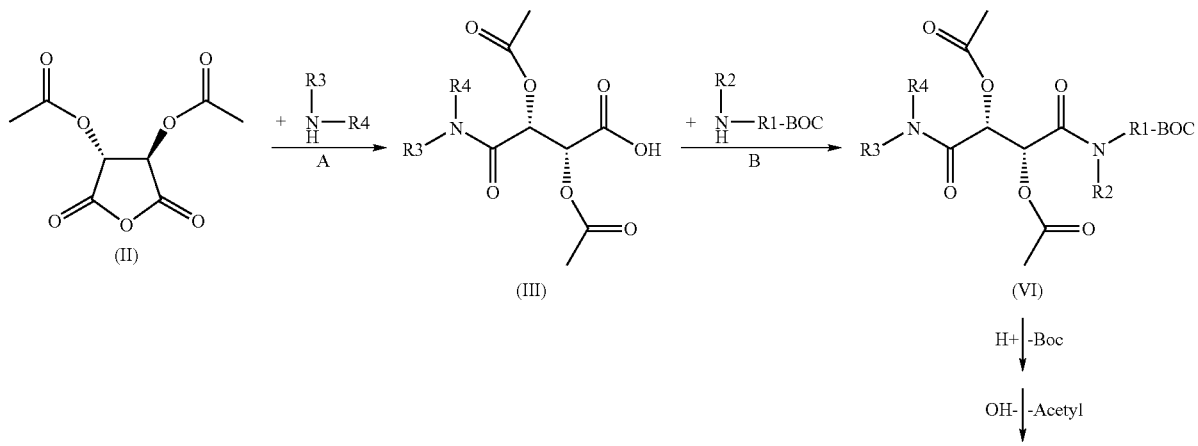

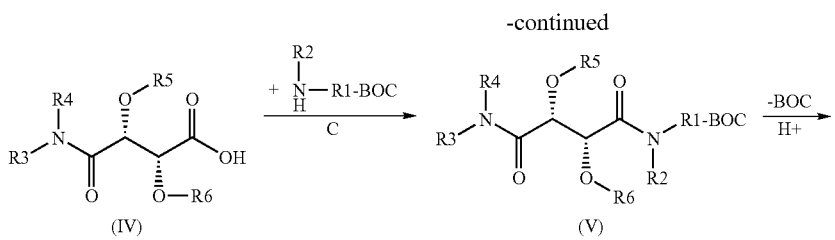
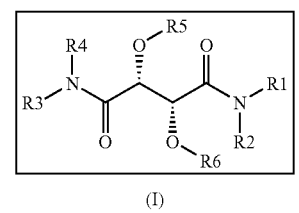

The radicals R1, R2, R3 and R4 used in Scheme 1 have the same meaning as those in the compound of the formula I; BOC is the protective group butoxycarbonyl. In a process step A, diacetyl-L-tartaric anhydride (compound of the formula II) is dissolved in a solvent such as dimethylformamide (DMF), tetrahydrofuran (THF), N-methylpyrrolidinone (NMP), dioxane or dichloromethane and reacted with a suitable amine of the formula NH(R3)-R4 to give the corresponding amide (III). For this, a suitable base such as N-methylmorpholine or alternatively another amine base such as Hünig's base, triethylamine (NEt$_3$) or 4-dimethylaminopyridine (4-DMAP) is added. In the next step B, the monoamide III is dissolved in a solvent such as dimethylformamide (DMF), tetrahydrofuran (THF), NMP, dioxane or dichloromethane and coupled with a suitable amine of the formula NH(R1-BOC)—R2 to give the corresponding diamide (VI). For this, as described above, a customary coupling reagent such as TOTU, PyBrop, PyBop, HATU or EDC and a suitable base such as amine bases such as Hünig's Base, NEt$_3$ or DMAP are used.

After removal of protective groups such as the Boc protective group on N(R1)-R2 using standard methods such as using TFA-CH$_2$Cl$_2$ and removal of the acetyl groups by basic hydrolysis, for example using NaOH at room temperature (RT), the target compounds (1) are obtained. (For alternative methods for the removal of protective groups see, for example, Kocienski, P. J., *Protecting groups*, Thieme Verlag 1994, pp. 1-16). This route affords compounds of the type I where R6=H. Compounds where R6 is not equal to H can in principle be prepared from these according to known standard processes (for example ester formation or carbamoylations)

In an alternative process (C), a tartaric acid monoamide (IV) is dissolved directly in a solvent such as dimethylformamide (DMF), tetrahydrofuran (THF), NMP, dioxane or CH$_2$Cl$_2$ and coupled with a suitable amine of the formula NH(R1-BOC)—R2 to give the corresponding diamide (V). For this, a customary coupling reagent such as TOTU, PyBrop, PyBop, Hatu or EDC and a suitable base such as amine bases such as Hünig's Base, NEt$_3$ or DMAP are used. After the removal of protective groups such as the BOC protective groups on N(R1)-R2 using standard methods, for example TFA-CH$_2$Cl$_2$ at RT, the target compounds (1) are obtained. Compounds where R6 is not equal to H can in principle also be prepared according to this process.

The invention further relates to a process for the preparation of the compound of the formula I and/or of a stereoisomeric form of the compound of the formula I and/or of a physiologically tolerable salt of the compound of the formula I, which comprises a) reacting a compound of the formula II

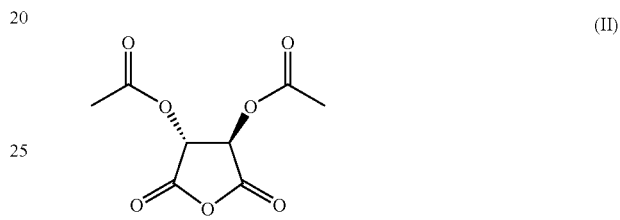

with a compound NH(R3)(R4) to give a compound of the formula III,

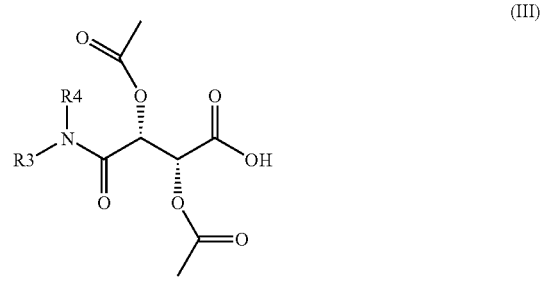

where the radicals R3 and R4 are as defined in formula I, and reacting the compound of the formula III with a compound NH(R2)(R1)-Boc to give a compound of the formula VI,

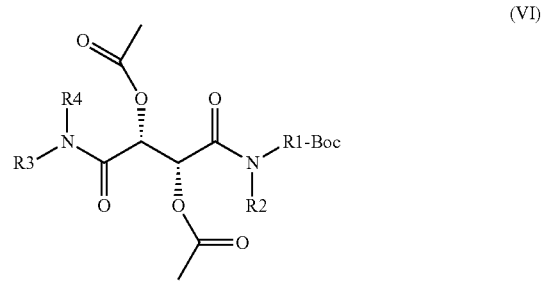

where the radicals R1, R2, R3 and R4 are as defined in formula I and Boc is the protective group butoxycarbonyl, and subsequently reacting to give a compound of the formula I, or b) reacting a compound of the formula IV

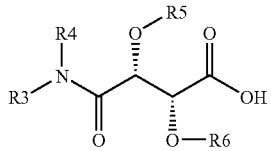

(IV)

where the radicals R3, R4, R5 and R6 are as defined in formula I, with a compound NH(R2)(R1)-Boc to give a compound of the formula V,

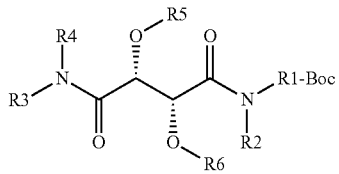

(V)

where the radicals R1, R2, R3, R4, R5 and R6 are as defined in formula I and Boc is the protective group butoxycarbonyl, and subsequently reacting to give a compound of the formula I, or c) either isolating the compound of the formula I prepared according to process a) or b) in free form or releasing it from physiologically intolerable salts or, in the case of the presence of acidic or basic groups, converting it to physiologically tolerable salts, or d) separating a compound of the formula I prepared according to process a) or b), or a suitable precursor of the formula I, which on account of its chemical structure occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

A compound of the formula I prepared according to Scheme 1, or a suitable precursor of the formula I which on account of its chemical structure occurs in enantiomeric forms, can be separated into the pure enantiomers (process d) by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups, or the compound of the formula I prepared according to Scheme 1 can either be isolated in free form or, in the case of the presence of acidic or basic groups, converted to physiologically tolerable salts (process c).

In process d), the compound of the formula I, if it occurs as a mixture of diastereomers or enantiomers or is obtained in the chosen synthesis as mixtures thereof, is separated into the pure stereoisomers, either by chromatography on an optionally chiral support material, or, if the racemic compound of the formula I is capable of salt formation, by fractional crystallization of the diastereomeric salts formed using an optically active base or acid as an auxiliary. Suitable chiral stationary phases for the thin-layer or column-chromatographic separation of enantiomers are, for example, modified silica gel supports ("Pirkle phases") and high molecular weight carbohydrates such as triacetylcellulose. For analytical purposes, gas chromatographic methods on chiral stationary phases can also be used after appropriate derivatization known to the person skilled in the art. For the separation of the enantiomers of the racemic carboxylic acids, the diastereomeric salts of differing solubility are formed using an optically active, usually commercially obtainable, base such as (−)-nicotine, (+)- and (−)-phenylethylamine, quinine bases, L-lysine or L- and D-arginine, the more poorly soluble component is isolated as a solid, the more readily soluble diastereomer is precipitated from the mother liquor and the pure enantiomers are obtained from the diastereomeric salts thus obtained. In a manner which is identical in principle, the racemic compounds of the formula I, which contain a basic group such as an amino group, can be converted into the pure enantiomers using optically active acids, such as (+)-camphor-10-sulfonic acid, D- and L-tartaric acid, D- and L-lactic acid and (+) and (−)-mandelic acid. Chiral compounds which contain alcohol or amine functions can also be converted using appropriately activated or optionally N-protected enantiomerically pure amino acids to the corresponding esters or amides, or conversely chiral carboxylic acids can be converted using carboxy-protected enantiomerically pure amino acids to the amides or, using enantiomerically pure hydroxycarboxylic acids such as lactic acid, to the corresponding chiral esters. Then, the chirality of the amino acid or alcohol radical introduced in enantiomerically pure form can be used for the separation of the isomers, by carrying out a separation of the diastereomers now present by crystallization or chromatography on suitable stationary phases and then removing the entrained chiral moiety again by means of suitable methods.

Furthermore, in the case of some of the compounds according to the invention the possibility arises of employing diastereomerically or enantiomerically pure starting products for the preparation of the ring structures. By this means, other or simplified processes can be employed for the purification of the final products. These starting products were prepared beforehand in enantiomerically or diastereomerically pure form according to processes known from the literature. This can mean, in particular, that in the synthesis of the skeletal structures either enantioselective processes are used, or else an enantiomeric (or diastereomeric) separation is carried out at an earlier stage of the synthesis and not only at the stage of the final products. Likewise, a simplification of the separations can be achieved by proceeding in two or more stages.

Acidic or basic products of the compound of the formula I can be present in the form of their salts or in free form. Pharmacologically tolerable salts are preferred, for example alkali metal or alkaline earth metal salts such as hydrochlorides, hydrobromides, sulfates, hemisulfates, all possible phosphates, and salts of the amino acids, natural bases or carboxylic acids.

The preparation of physiologically tolerable salts from compounds of the formula I capable of salt formation, including their stereoisomeric forms, according to process step c) is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the formula I form stable alkali metal, alkaline earth metal or optionally substituted ammonium salts. If the compounds of the formula I have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments which comprise an efficacious amount of at least one compound of the formula I and/or of a physiologically tolerable salt of the compound of the formula I and/or an optionally stereoisomeric form of the compound of the formula I, together with a pharmaceutically suitable and physiologically tolerable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the formula I can be employed in patients who are suffering from disorders of well-being or diseases which accompany thromboses, embolisms, hypercoagulability or fibrotic changes. These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the formula I can be employed in all interventions which lead to contact of the blood with foreign surfaces, as in dialysis patients and patients with indwelling catheters. Compounds of the formula I can also be employed in order to reduce the risk of thrombosis after surgical interventions such as in knee and hip joint operations.

Compounds of the formula I are suitable for the treatment of patients with disseminated intravascular coagulation, sepsis and other intravascular events which accompany inflammation. Furthermore, compounds of the formula I are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the formula I are suitable for the retardation or prevention of such processes.

Further indications for the use of the compounds of the formula I are fibrotic changes of the lungs such as chronic obstructive pulmonary disease, adult respiratory distress syndrome (ARDS) and of the eye, such as fibrin deposits after eye operations. Compounds of the formula I are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for the production of a medicament, which comprises bringing at least one compound of the formula I into a suitable administration form using a pharmaceutically suitable and physiologically tolerable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the formula I according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to formula I, daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the formula I can be administered both as a monotherapy and in combination or together with all antithrombotics (anticoagulants and platelet aggregation inhibitors), thrombolytics (plasminogen activators of any type), other profibrinolytically active substances, hypotensives, blood sugar regulators, lipid-lowering agents and antiarrhythmics.

EXAMPLES

Final products are usually determined by mass spectroscopic methods (FAB, ESI-MS) and $^1$H-NMR, in each case the main peak or the two main peaks are indicated. Temperature data in degrees Celsius, Yld. is yield. Abbreviations used are either explained or correspond to the customary conventions.

If not stated otherwise, chromatographic separations were carried out on silica gel using ethyl acetate/heptane mixtures as eluents. Preparative separations on reversed phase (RP) silica gel (HPLC) were carried out, if not stated otherwise, under the following conditions: column Merck Hibar RT 250-25 Lichrospher 100 RP-18e 5 μm, Merck KGaA, Germany, Life Science & Analytics, 64293 Darmstadt; mobile phase A: $H_2O$+0.1% TFA, phase B: 80% acetonitrile+0.1% TFA, flow 25 ml/min., 0 to 7 min. 100% A, 7 to 22 min. to 100% B, 22 to 30 min. 100% B, 30 to 33 min. to 100% A, 33 to 35 min. 100% A.

The evaporation of solvents was usually carried out under reduced pressure at 35° C. to 45° C. on a rotary evaporator. If not mentioned otherwise, the LC/MS analyses were carried out under the following conditions:

Method A:

| | |
|---|---|
| Column: | YMC J'shere H80 33 × 2.1 mm; Waters GmbH, Helfmann-Park 10, 65760 Eschborn, Germany; packing material 4 μm, |
| Solvent: | ACN + 0.05% TFA:H$_2$O + 0.05% TFA (flow 1.3 ml/min) |
| Gradient: | 5:95 (0 min) to 95:5 (2.5 min) to 95:5 (3.0 min) |
| Ionization: | ESI$^+$ |

Method B:

| | |
|---|---|
| Column: | YMC J'shere H80 33 × 2.1 mm; packing material 4 μm, |
| Solvent: | ACN + 0.05% TFA:H$_2$O + 0.05% TFA (flow 1 ml/min) |
| Gradient: | 5:95 (0 min) to 95:5 (3.4 min) to 95:5 (4.4 min) |
| Ionization: | ESI$^+$ |

Method D:

| | |
|---|---|
| Column: | YMC J'shere ODS H80 20 × 2.1 mm packing material 4 μm, |
| Solvent: | ACN:H$_2$O + 0.05% TFA (flow 1 ml/min) |
| Gradient: | 4:96 (0 min) to 95:5 (2 min) to 95:5 (2.4 min) to 96:4 (2.45 min) |
| Ionization: | ESI$^+$ |

Preparative HPLC was carried out using the following method:

| | |
|---|---|
| Column: | Waters Atlantis dC18 OBD 30 × 100 mm 5 μm; Waters GmbH, Helfmann-Park 10, 65760 Eschborn, Germany |
| Solvent: | ACN:H$_2$O + 0.1% TFA (flow 60 ml/min) |
| Gradient: | 10:90 (0 min) to 90:10 (10 min) |

Abbreviations Used:
ACN acetonitrile
Boc butoxycarbonyl
DCM dichloromethane
(DHQ)$_2$PHAL 1-[(R)-((4S,5R)-5-ethyl-1-azabicyclo[2.2.2]oct-2-yl)-(6-methoxy-quinolin-4-yl)methoxy]-4-[(R)-((4R,5S)-5-ethyl-1-azabicyclo-[2.2.2]oct-2-yl)-(6-methoxyquinolin-4-yl)methoxy]phthalazine
DIPEA N,N-diisopropylethylamine (Hünig's base)
DMF dimethylformamide
DMSO dimethyl sulfoxide
EDC N'-(3-dimethylaminopropyl)-N-ethylcarbodiimide
HATU O-(7-azabenzotriazol-1-yl)-N,N,N',N'-tetramethyluronium hexafluorophosphate
HOAt 1-hydroxy-7-azabenzotriazole
K$_2$[OsO$_2$(OH)$_4$] potassium osmate dihydrate
LC/MS liquid chromatography-mass spectroscopy
MeOH methanol
NMM N-methylmorpholine
PyBop 1-benzotriazolyloxytripyrrolidinophosphonium hexafluoro-phosphate
PyBrop bromotrispyrrolidinephosphonium hexafluorophosphate
R$_t$ retention time
TDBTU O-(3,4-dihydro-4-oxo-1,2,3-benzotriazin-3-yl)-N,N,N',N'-tetramethyluronuim tetrafluoroborate
TFA trifluoroacetic acid
TOTU O-((ethoxycarbonyl)cyanomethylenimino)-N,N,N',N'-tetramethyluronium tetrafluoroborate
RT room temperature (21° C. to 24° C.)

Example 1

(2R,3R)—N-(1-Aminoisoquinolin-6-yl)-2,3-dihydroxy-N'-p-tolyltartaramide; compound with trifluoroacetic acid

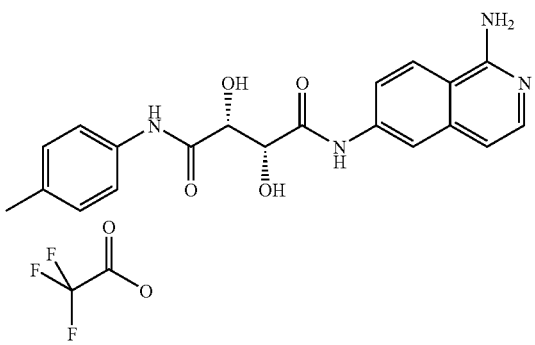

Process Step 1:

[6-((2R,3R)-2,3-Dihydroxy-3-p-tolylcarbamoylpropionylamino)isoquinolin-1-yl]-N-di-carboxyamino tertiary-butyl ester

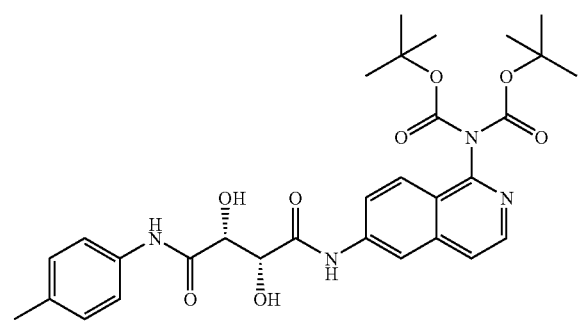

0.037 ml of NMM (0.334 mmol) were added to a solution of 26.6 mg of (2R,3R)-2,3-dihydroxy-N-p-tolyltartaric acid (0.111 mmol), 40.0 mg of 6-aminoisoquinolin-1-yl)-N-dicarboxyamino tertiary-butyl ester (0.111 mmol) (6-aminoisoquinolin-1-yl)-N-di-carboxyamino tert-butyl ester was obtained as in the process described in WO2004/072101, page 108) and 15.1 mg of HOAt (0.111 mmol) in 1.5 ml of DMF and the mixture was stirred for 10 min. After the addition of 52 mg of PyBrop (0.111 mmol), the reaction mixture was stirred at RT for 42 hours (h). The reaction mixture was filtered and purified by means of preparative HPLC. The purified fractions of the product were lyophilized. 4 mg of a white solid were obtained.

Yield: 6% LC/MS (Method D) (M+H)$^+$ 581

Process Step 2:

(2R,3R)—N-(1-Aminoisoquinolin-6-yl)-2,3-dihydroxy-N'-p-tolyltartaramide; compound with trifluoroacetic acid 1 ml of TFA was added to a solution of the compound obtained from Process step 1 (4 mg, 6.9 μmol) in 3 ml of DCM and the mixture was stirred at RT for 2 h. The solvents were distilled off under reduced pressure, the residue was dissolved in MeOH and water, the solution was subsequently lyophilized overnight and 4 mg of the title compound were obtained as a white solid. Purity 85%.

LC/MS (Method B) 380.15 ($R_t$=1.05 min, 97%)

$^1$H NMR (500 MHz, DMSO-$d_6$) δ (ppm): 1.73 (impurity), 2.26 (s, 3H), 3.01 (impurity), 4.51 (dd, 1H), 4.57 (dd, 1H), 6.05 (d, 1H), 6.22 (d, 1H), 7.13 (d, 2H), 7.18 (d, 1H), 7.62 (m, 3H), 8.04 (dd, 1H), 8.48 (q, 2H), 8.76 (s, 2H), 9.55 (s, 1H), 10.29 (s, 1H), 12.71 (s, 1H)

Example 2

(2R,3R)—N-(2-Amino-3H-benzimidazol-5-yl)-2,3-dihydroxy-N'-p-tolyltartaramide; compound with trifluoroacetic acid

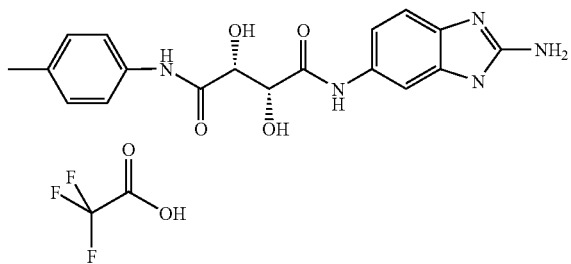

Process Step 1:

(2R,3R)-2-Amino-6-(2,3-dihydroxy-3-p-tolylcarbamoylpropionylamino)-benzimidazole-1-carboxyamino tertiary-butyl ester

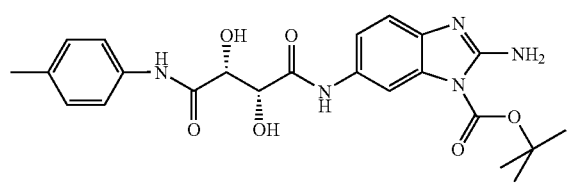

119 mg of (2R,3R)-2,3-dihydroxy-N-p-tolyltartaric acid (0.5 mmol) and 124 mg of tertiary-butyl 2,5-diaminobenzimidazole-1-carboxylate (0.5 mmol) (tertiary-butyl 2,5-diamino-N-Boc-benzimidazole-1-carboxylate was prepared according to International application WO2002/042273) were dissolved in 5 ml of DMF. 74 mg of HOAt (0.55 mmol), 180 mg of PyBrop (0.55 mmol) and 193 mg of DIPEA (1.5 mmol) were dissolved in a mixture of 1.5 ml of DCM and 1.5 ml of DMF and added to the reaction mixture. After stirring overnight, the mixture was diluted with ethyl acetate. The organic phase was washed with an aqueous sodium hydrogencarbonate solution and common salt solution, dried over sodium sulfate, filtered and the solvents were removed under reduced pressure. The title compound was obtained as an oil.

LC/MS (Method D) (M+H-tBu)$^+$ 414

Process Step 2:

(2R,3R)—N-(2-Amino-3H-benzimidazol-5-yl)-2,3-dihydroxy-N'-p-tolyltartaramide; compound with trifluoroacetic acid The residue from Process step 1 was dissolved in a mixture of 2 ml of DCM and 2 ml of TFA. After stirring at RT for 2 h, the solvents were removed under reduced pressure and purified using HPLC. 90 mg (Yield: 37%) of the title compound were obtained as a white solid.

LC/MS (Method A) 370.15 ($R_t$=1.0 min, 100%)

$^1$H NMR (400 MHz, DMSO-$d_6$) δ (ppm): 2.23 (s, 3H), 4.47 (t, 2H), 6.00 (dd, 2H), 7.12 (d, 2H), 7.28 (s, 1H), 7.48 (d, 1H), 7.62 (d, 2H), 8.03 (s, 1H), 8.39 (s br, 2H), 9.51 (s, 1H), 9.78 (s, 1H)

Example 3

(2R,3R)—N-(2-Amino-3H-benzimidazol-5-yl)-N'-(4-cyclohexylphenyl)-2,3-dihydroxy-tartaramide; compound with trifluoroacetic acid

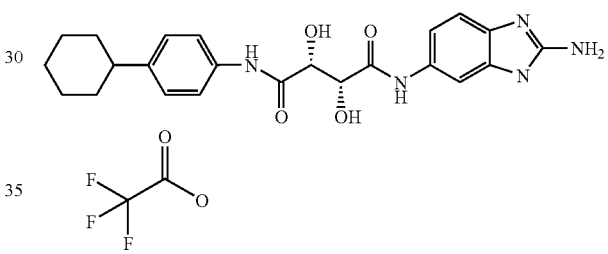

Process Step 1:

(2R,3R)-2,3-Diacetoxy-N-(4-cyclohexylphenyl)tartaric acid

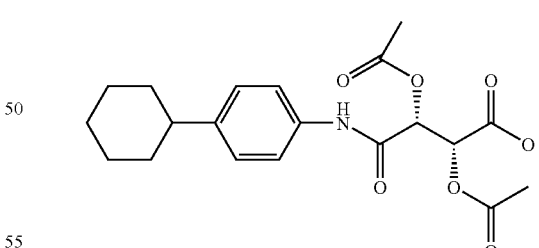

216 mg of (+)-diacetyl-L-tartaric anhydride (1 mmol) and 263 mg of 4-cyclohexyl-phenylamine (1.5 mmol) and 200 µl of N-methylmorpholine were dissolved in 5 ml of DMF and the mixture was stirred for 3 h at RT. The mixture was diluted with ethyl acetate. The organic phase was washed with 1 N HCl solution and common salt solution, dried over sodium sulfate, filtered and the solvents were removed under reduced pressure. 430 mg of the title compound were obtained as an oil (Yield approximately 100%). LC/MS (Method D) (M+H)$^+$ 392

Process Step 2:

tertiary-Butyl (2R,3R)-2-amino-6-[2,3-d]acetoxy-3-(4-cyclohexylphenylcarbamoyl)-propionylamino)-benzimidazole-1-carboxylate

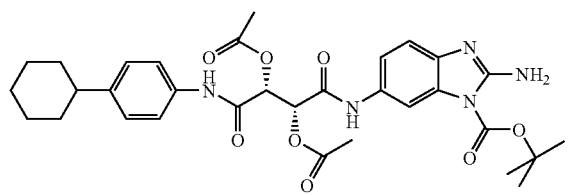

118 mg of the compound obtained from Process step 1 (0.3 mmol) and 110 µl of N-methylmorpholine were dissolved in 2 ml of DMF at 0° C. 115 mg of TDBTU (0.33 mmol) were added and the mixture was stirred for a further 30 min. 82 mg of tertiary-butyl 2,5-diaminobenzimidazole-1-carboxylate (0.33 mmol) were added and the mixture was stirred at 0° C. for 4 h. The mixture was diluted with ethyl acetate. The organic phase was washed with aqueous sodium hydrogencarbonate solution and common salt solution, dried over sodium sulfate, filtered and the solvents were removed under reduced pressure. The title compound was obtained as an oil. LC/MS (Method D) (M+H)$^+$ 622

Process Step 3:

(2R,3R)-2-Acetoxy-2-(2-amino-3H-benzimidazol-5-ylcarbamoyl)-1-(4-cyclohexyl-phenylcarbamoyl) ethyl acetate; compound with trifluoroacetic acid

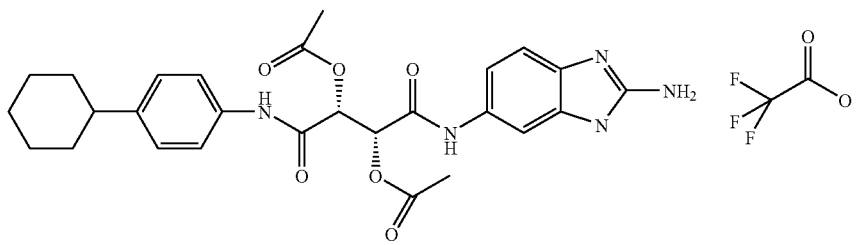

The compound from Process step 2 was dissolved in 3 ml of DCM and 1.5 ml of TFA and the mixture was stirred at RT for 2 h. The title compound was obtained as an oil.

Process Step 4:

(2R,3R)—N-(2-Amino-3H-benzimidazol-5-yl)-N'-(4-cyclohexylphenyl)-2,3-dihydroxy-tartaramide; compound with trifluoroacetic acid The oil from Process step 3 was dissolved in 3 ml of methanol and treated with 500 µl of 5 N NaOH overnight. The solvents were distilled off under reduced pressure and the residue was dissolved in 2 ml of TFA and evaporated. The residue was purified by means of HPLC and 7 mg of the title compound were obtained as a white solid. LC/MS (Method A) 437.21 (R$_t$=1.39 min, 100%)

$^1$H NMR (400 MHz, DMSO-d$_6$) δ (ppm): 1.16-1.42 (m, 5H), 1.68-1.83 (m, 5H), 4.49 (dd, 2H), 5.99 (dd, 2H), 7.17 (d, 2H), 7.25 (d br, 1H), 7.45 (d, 1H), 7.62 (d, 2H), 8.02 (s br, 1H), 8.36 (s br, 2H), 9.53 (s, 1H), 9.78 (s, 1H)

Example 4

(2R,3R)—N-(4-Aminomethylphenyl)-2,3-dihydroxy-N'-p-tolylsuccinamide; compound with trifluoroacetic acid

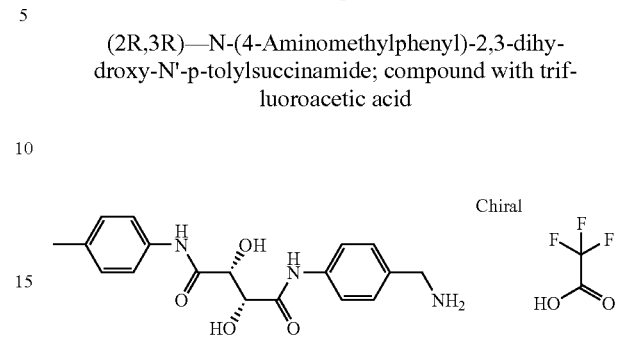

Process Step 1:

tert-Butyl[4-((2R,3R)-2,3-dihydroxy-3-p-tolylcarbamoylpropionylamino)benzyl]-carbamate

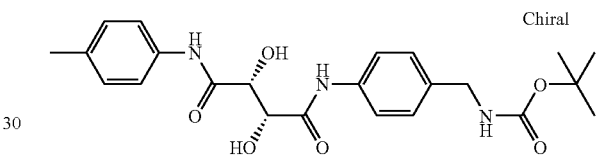

In analogy to Example 1, Process step 1, 33 mg (0.15 mmol) of tert-butyl (4-aminobenzyl)carbamate and 36 mg (0.15 mmol) of (2R,3R)-2,3-dihydroxy-N-p-tolyl-succinic acid were dissolved in 1 ml of DCM and 1 ml of DMF and treated successively with 78 µl of DIPEA (0.45 mmol), 22.5 mg of HOAt (0.165 mmol) and 76.9 mg (0.165 mmol) of PyBrop. Without further work-up, the batch obtained was filtered and purified by means of HPLC. The product-containing fractions were lyophilized.

Process Step 2:

(2R,3R)—N-(4-Aminomethylphenyl)-2,3-dihydroxy-N'-p-tolylsuccinamide; compound with trifluoroacetic acid

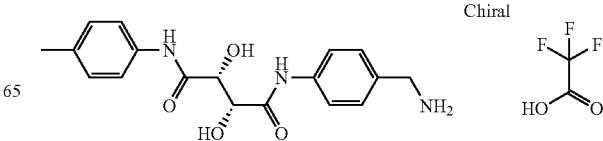

The process product from step 1 was reacted analogously to Example 1; Process step 2, then the mixture was concentrated, treated with water and lyophilized.

Yield: 15.5 mg (23% over 2 stages).

LC/MS (Method A) M-NH$_2$=327.36 (R$_t$=0.88 min, 93%)

$^1$H NMR (500 MHz, DMSO-d$_6$) δ (ppm): 2.25 (s, 3H), 3.98 (s br, 2H), 4.49 (m, 2H), 5.99 (d, 1H), 6.09 (d, 1H), 7.12 (d, 2H), 7.39 (d, 2H), 7.62 (d, 2H), 7.79 (d, 2H), 8.12 (s br, 3H), 9.51 (s, 1H), 9.72 (s, 1H).

Example 5

(2R,3R)—N-(4-Carbamimidoylphenyl)-2,3-dihydroxy-N'-p-tolylsuccinamide; compound with trifluoroacetic acid

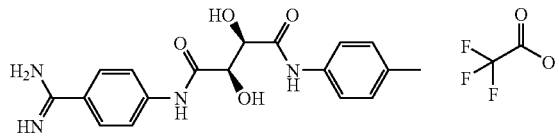

Process Step 1:

(2R,3R)-2,3-Diacetoxy-N-(4-carbamimidoylphenyl)succinic acid; compound with trifluoroacetic acid

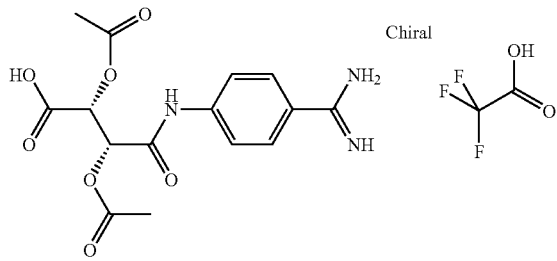

500 mg (2.39 mmol) of 4-aminobenzamidine dihydrochloride and 519 mg (2.40 mmol) of (3R,4R)-4-acetoxy-2,5-dioxotetrahydrofuran-3-yl acetate were dissolved in 2 ml of pyridine and 2 ml of DMF and treated with 25 mg of 4-DMAP. The mixture was then heated for 1 h at 100° C. The mixture was filtered and purified using HPLC. The product-containing fractions were combined and lyophilized.

Yield: 130 mg (12%).

Process Step 2:

(2R,3R)—N-(4-Carbamimidoylphenyl)-2,3-dihydroxy-N'-p-tolylsuccinamide; compound with trifluoroacetic acid

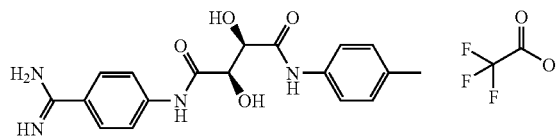

52 mg (0.11 mmol) of the derivative obtained in Process step 1 were dissolved in 1 ml of DMF and subsequently treated with 15 mg (0.13 mmol) of toluidine, 62 mg (0.13 mmol) of PyBrop, 18 mg (0.13 mmol) of HOAt and 65 μl (0.58 mmol) of NMM. After stirring at RT for 1 h, 2 ml of MeOH and 90 mg of sodium methoxide were added. After conversion was complete, the mixture was filtered and purified by means of HPLC.

Yield: 19 mg (36% over 2 stages).

LC/MS (Method A) 357.43 (R$_t$=0.88 min, 100%)

$^1$H NMR (500 MHz, DMSO-d$_6$) δ (ppm): 2.26 (s, 3H), 4.48 (m, 1H), 4.53 (m, 1H), 6.01 (m, 1H), 6.16 (m, 1H), 7.13 (d, 2H), 7.63 (d, 2H), 7.81 (d, 2H), 8.01 (d, 2H), 8.86 (s br, 2H), 9.20 (s br, 2H), 9.53 (s, 1H), 10.13 (s, 1H).

The compounds in Table 1 below were prepared in a manner analogous to the above examples.

TABLE 1

| Example No. | Structure | Mass from LC-MS | R$_t$ from LC-MS | LC-MS method |
|---|---|---|---|---|
| 6 | 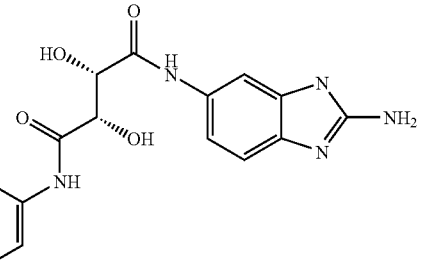 | 374.19 | 0.88 | A |

TABLE 1-continued
| Example No. | Structure | Mass from LC-MS | $R_t$ from LC-MS | LC-MS method |
|---|---|---|---|---|
| 7 | 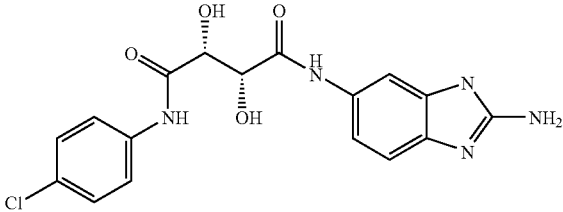 | 390.16 | 1.02 | A |
| 8 | 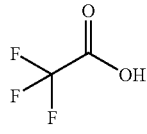 Chiral | 356.17 | 0.84 | A |
| 9 | 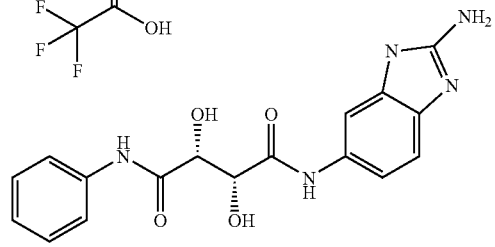 | 401.18 | 0.99 | A |
| 10 | 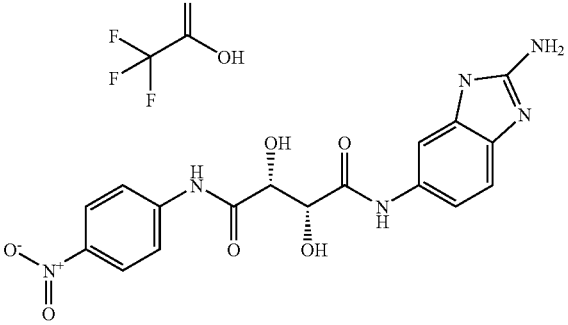 Chiral | 398.17 | 1.2 | A |

TABLE 1-continued

| Example No. | Structure | Mass from LC-MS | $R_f$ from LC-MS | LC-MS method |
|---|---|---|---|---|
| 11 | 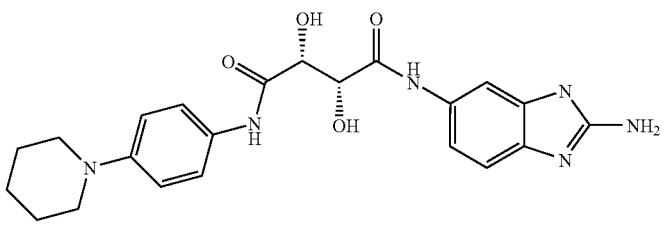 | 439.24 | 0.65 | A |
| 12 | 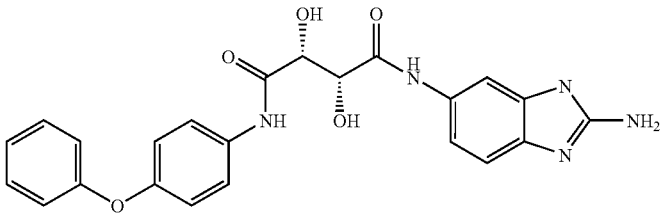 | 448.14 | 1.28 | A |

Pharmacological Examples

Factor IXa Determination Method

The prepared substances from the examples were tested for inhibition of the enzymatic activity of FIXa using the substrate PEFA 3107 (Pentapharm/Loxo; via S. Black GmbH, Baumstrasse 41, 47198 Duisburg, Germany; Pr. No. 095-20) and factor IXa (Calbiochem, Merck KGaA markets Calbiochem in Germany, Life Science & Analytics, 64293 Darmstadt; Pr. No. 233290). In this method, 28 µl of test buffer (50 mM α,α,α-tris(hydroxymethyl)methylamine (TRIS), 100 mM NaCl, 5 mM $CaCl_2$, 0.1% bovine serum albumin, pH 7.4) and 10 µl of factor IXa (277 nM final concentration in the test batch) were added to 2 µl of 10 mM dimethyl sulfoxide solution of the respective test substance, and the mixture was incubated for 15 minutes at room temperature in a 96 half-well microtiter plate. The enzyme reaction was started by addition of 10 µl of substrate (1 mM stock solution in water). The time course of the reaction was monitored at 405 nm in a microtiter plate reader (SpectraMax plus 384; Molecular Devices) for 15 minutes.

The $IC_{50}$ was calculated from the averaged values (duplicate determination) of a dilution series of the test substance with the aid of the software Grafit 4 (Erithacus Software, UK). The inhibition constants ($K_i$) were calculated according to the Cheng Prusoff equation $Ki=IC_{50}/(1+(S/Km))$, where S=concentration of the test substrate in the test and $K_m$=Michaelis-Menten constant.

Table 2 shows the results.

TABLE 2

| Compound from Example | Factor IXa enzyme assay $IC_{50}$ [micro M] |
|---|---|
| 1 | 0.22 |
| 5 | 0.17 |
| 12 | 0.37 |

What is claimed is:
1. A compound of formula I

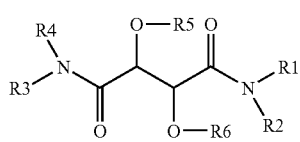

(I)

or a stereoisomeric form of a compound of formula I, or a mixture of such forms in any ratio, or a physiologically tolerable salt of a compound of formula I
where
R1 is carbamimidoylphenyl, aminomethylphenyl or Het-Z, where Het is selected from the group consisting of benzimidazolyl and isoquinolinyl, and in which Z is amino or amidino,
R2 and R4 are in each case a hydrogen atom, R3 is
1) phenyl, in which phenyl is unsubstituted or mono- or disubstituted by T,
2) -phenyl-Q-phenyl, in which the two phenyl radicals in each case independently of one another are unsubstituted or mono- or disubstituted by T or
3) phenyl-Q-Het-2, in which Het-2 is selected from the group consisting of quinolinyl, quinoxalinyl, furanyl, indolyl, isoquinolinyl, isothiazolyl, isoxazolyl, oxadiazolyl, piperidinyl, pyrazolyl, pyridazinyl, pyrimidinyl, pyridyl, pyrimidinyl, pyrrolyl, thiadiazolyl, thiazolyl, thienyl, thienopyrrolyl or thienothiophenyl, and in which phenyl and Het-2 in each case independently of one another are unsubstituted or mono- or disubstituted by T, Q is a covalent bond, $-CH_2-$, $-N(CH_3)-$ or $-O-$, T is
1) F, Cl or Br,
2) $-(C_1-C_4)$-alkyl, in which alkyl are unsubstituted or independently mono- or disubstituted by $-CF_3$ or $-N-C(O)-CH_3$, or
3) $-NO_2$, and R5 and R6 are in each case a hydrogen atom.

2. A compound of formula I as claimed in claim 1 which is the compound (2R,3R)—N-(1-aminoisoquinolin-6-yl)-2,3-dihydroxy-N'-p-tolylsuccinamide, (2R,3R)—N-(2-amino-3H-benzimidazol-5-yl)-2,3-dihydroxy-N'-p-tolyl-succinamide, (2R,3R)—N-(2-amino-3H-benzimidazol-5-yl)-N-(4-cyclohexylphenyl)-2,3-dihydroxysuccinamide, (2R,3R)—N-(4-aminomethylphenyl)-2,3-dihydroxy-N'-p-tolylsuccinamide, (2R,3R)—N-(4-carbamimidoylphenyl)-2,3-dihydroxy-N'-p-tolylsuccinamide, (2R,3R)—N-(2-amino-3H-benzimidazol-5-yl)-N'-(4-fluorophenyl)-2,3-dihydroxysuccinamide, (2R,3R)—N-(2-amino-3H-benzimidazol-5-yl)-N-(4-chlorophenyl)-2,3-dihydroxysuccinamide, (2R,3R)—N-(2-amino-3H-benzimidazol-5-yl)-2,3-dihydroxy-N'-phenyl-succinamide, (2R,3R)—N-(2-amino-3H-benzimidazol-5-yl)-2,3-dihydroxy-N'-(4-nitrophenyl)-succinamide, (2R,3R)—N-(2-amino-3H-benzimidazol-5-yl)-2,3-dihydroxy-N'-(4-isopropyl-phenyl)succinamide, (2R,3R)—N-(2-amino-3H-benzimidazol-5-yl)-2,3-dihydroxy-N'-(4-piperidin-1-yl-phenyl)succinamide or (2R,3R)—N-(2-amino-3H-benzimidazol-5-yl)-2,3-dihydroxy-N-(4-phenoxy-phenyl)succinamide.

3. A medicament comprising an efficacious amount of at least one compound of formula I as claimed in claim 1 together with a pharmaceutically suitable and physiologically tolerable vehicle, additive or other active substances and auxiliaries.

* * * * *